(12) United States Patent
Bono et al.

(10) Patent No.: US 11,547,495 B2
(45) Date of Patent: Jan. 10, 2023

(54) SYSTEM AND METHOD FOR REDUCING INTERFERENCE IN POSITIONAL SENSORS FOR ROBOTIC SURGERY

(71) Applicant: GLOBUS MEDICAL, INC., Audubon, PA (US)

(72) Inventors: Peter L. Bono, Bingham Farms, MI (US); James D. Lark, West Bloomfield, MI (US); John S. Scales, Ann Arbor, MI (US); Thomas J. Lord, South Milwaukee, WI (US)

(73) Assignee: Globus Medical, Inc., Audubon, PA (US)

( * ) Notice: Subject to any disclaimer, the term of this patent is extended or adjusted under 35 U.S.C. 154(b) by 321 days.

(21) Appl. No.: 16/855,119

(22) Filed: Apr. 22, 2020

(65) Prior Publication Data

US 2020/0337783 A1 Oct. 29, 2020

Related U.S. Application Data

(60) Provisional application No. 62/839,023, filed on Apr. 26, 2019.

(51) Int. Cl.
*A61B 34/20* (2016.01)
*A61B 34/30* (2016.01)

(52) U.S. Cl.
CPC .............. *A61B 34/20* (2016.02); *A61B 34/30* (2016.02); *A61B 2034/2051* (2016.02); *A61B 2034/2065* (2016.02); *A61B 2034/2072* (2016.02)

(58) Field of Classification Search
CPC . A61B 34/20; A61B 34/30; A61B 2034/2051; A61B 2034/2065; A61B 2034/2072; A61B 2017/00725; A61B 2090/397; G01R 33/02
See application file for complete search history.

(56) References Cited

U.S. PATENT DOCUMENTS

| | | | | |
|---|---|---|---|---|
| 7,469,187 | B2 * | 12/2008 | Nieminen | A61B 34/20 702/38 |
| 8,040,127 | B2 * | 10/2011 | Jensen | A61B 34/20 324/207.16 |
| 9,522,045 | B2 * | 12/2016 | Ramachandran | A61B 34/20 |
| 2006/0116833 | A1 | 6/2006 | Nieminen et al. | |
| 2008/0079421 | A1 | 4/2008 | Jensen | |
| 2014/0354600 | A1 | 12/2014 | Ramachandran et al. | |

FOREIGN PATENT DOCUMENTS

| | | |
|---|---|---|
| EP | 1776923 | 4/2007 |
| EP | 1878384 | 1/2008 |
| EP | 1887309 | 2/2008 |

* cited by examiner

*Primary Examiner* — Joel Lamprecht

(57) ABSTRACT

The invention involves a system and method for increasing positional accuracy of surgical systems that utilize magnetic or electromagnetic sensors to provide positional awareness to a surgeon or robot performing the surgery. The system takes advantage of electromagnetic tracking through sensors. These sensors are very accurate and repeatable, while being compact enough to not inhibit surgical procedures. The accuracy and repeatability of the sensors is <1 mm within a predetermined 6 inch×6 inch performance motion box. The system is constructed and arranged to map the distortion patterns of the sensor and, in real time, correct the distortion pattern to provide accurate location of anatomical structures for performance of a surgery.

10 Claims, 3 Drawing Sheets

SYSTEM AND METHOD FOR REDUCING INTERFERENCE IN POSITIONAL SENSORS FOR ROBOTIC SURGERY

FIELD OF INVENTION

The present invention generally relates to robotic surgery and, more specifically, to a system and method for accounting for interference from objects causing electrical interference in locational sensors during robotic surgery.

BACKGROUND INFORMATION

Robotic surgery, computer-assisted surgery, and robotically-assisted surgery are terms for technological developments that use robotic systems to aid in surgical procedures. Robotically-assisted surgery was developed to overcome the limitations of pre-existing minimally-invasive surgical procedures and to enhance the capabilities of surgeons performing open surgery.

In the case of robotically-assisted minimally-invasive surgery, instead of directly moving the instruments, the surgeon uses one of two methods to control the instruments; either a direct telemanipulator or through computer control. A telemanipulator is a remote manipulator that allows the surgeon to perform the normal movements associated with the surgery while the robotic arms carry out those movements using end-effectors and manipulators to perform the actual surgery on the patient. In computer-controlled systems, the surgeon uses a computer to control the robotic arms and its end-effectors, though these systems can also still use telemanipulators for their input. One advantage of using the computerized method is that the surgeon does not have to be present, but can be anywhere in the world, leading to the possibility for remote surgery. One drawback of these systems relates to interference in the sensors that monitor the location of the robotic components, including the tools being used by the robot to complete the surgery. Surgical tools, and even robotic components, are often constructed from materials that are not radio translucent, and thus they cause interference with the sensors used to guide the robot to its desired precise location. The interference may cause the robot to not be located where it should be, and may cause problems with the surgery.

In the case of enhanced open surgery, autonomous instruments (in familiar configurations) replace traditional surgical tools, performing certain actions (such as rib spreading) with much smoother, feedback-controlled motions than could be achieved by a human hand. The main object of such smart instruments is to reduce or eliminate the tissue trauma traditionally associated with open surgery. This approach seeks to improve open surgeries, particularly orthopedic, that have so far not benefited from robotic techniques by providing a tool that can provide precise location of the tool with respect to anatomical markers when the robot or tool causes interference with the sensors used to provide that location.

One major drawback to electromagnetic sensors that can be used to provide positioning to robots for surgical procedures is their vulnerability to distortion. Materials with electromagnetic signatures impact the magnetic field which is generated by the NDI transmitter. This impact causes distortions in the sensor frame, which leads to incorrect position and orientation reporting.

There exists, therefore, a need for a robotic system that is capable of reducing or eliminating electrical and/or magnetic interference from tool and robot positioning to provide better positional accuracy.

Thus, the present invention provides a system and method for reducing distortion or interference during robotic or sensor enhanced manual surgery which overcomes the disadvantages of prior art systems.

SUMMARY OF THE INVENTION

Briefly, the invention involves a system and method for increasing positional accuracy of surgical systems that utilize electrical or magnetic sensors to provide positional awareness to a surgeon or robot performing the surgery. The system takes advantage of electromagnetic tracking through NDI sensors. These sensors are very accurate and repeatable, while being compact enough to not inhibit surgical procedures. The accuracy and repeatability of the sensors is <1 mm within a predetermined 6 inch×6 inch performance motion box. The system is constructed and arranged to map the distortion patterns of the sensor and, in real time, correct the distortion pattern to provide accurate location of anatomical structures for performance of a surgery.

Accordingly, it is an objective of the present invention to provide a system and method for reducing interference and distortion in positioning sensors used for surgical procedures.

It is a further objective of the present invention to provide a system and method for mapping the distortion patterns caused by objects placed into the surgical area.

It is yet a further objective of the present invention to provide a system and method for correcting distortion by recalling distortion patterns and comparing them to current distortion.

It is another objective of the present invention to provide a system and method of compensating for distortion in medical procedures that utilizes magnetic or electromagnetic sensors for anatomical positioning that learns from repeated occurrences of similar distortion.

Other objectives and advantages of this invention will become apparent from the following description taken in conjunction with the accompanying drawings, wherein are set forth, by way of illustration and example, certain embodiments of this invention. The drawings constitute a part of this specification, include exemplary embodiments of the present invention, and illustrate various objects and features thereof.

DETAILED DESCRIPTION OF THE PREFERRED EMBODIMENTS

Figure 1:
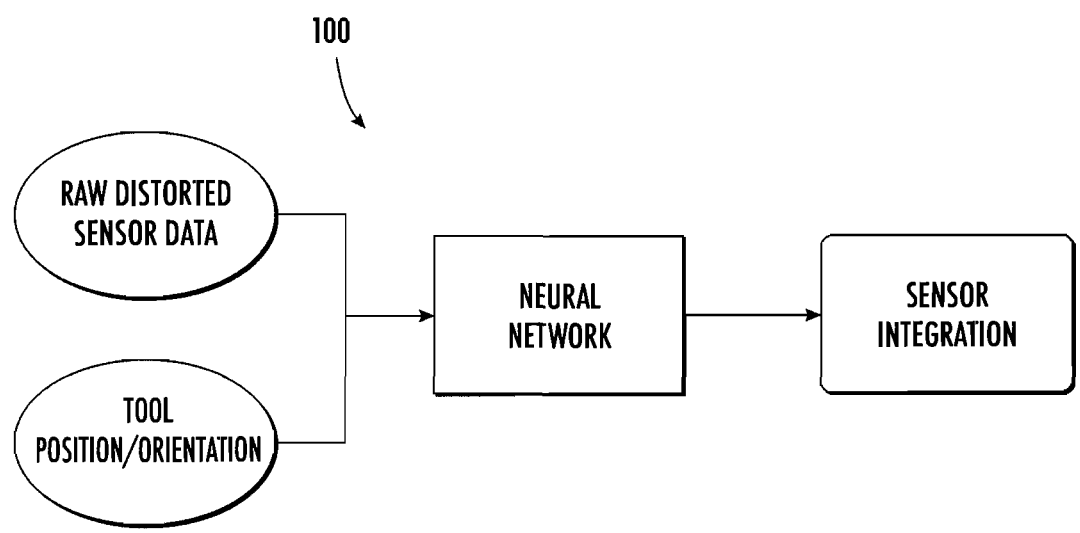
FIG. 1 is a schematic representation illustrating the flow of information of the present invention.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figure 2:
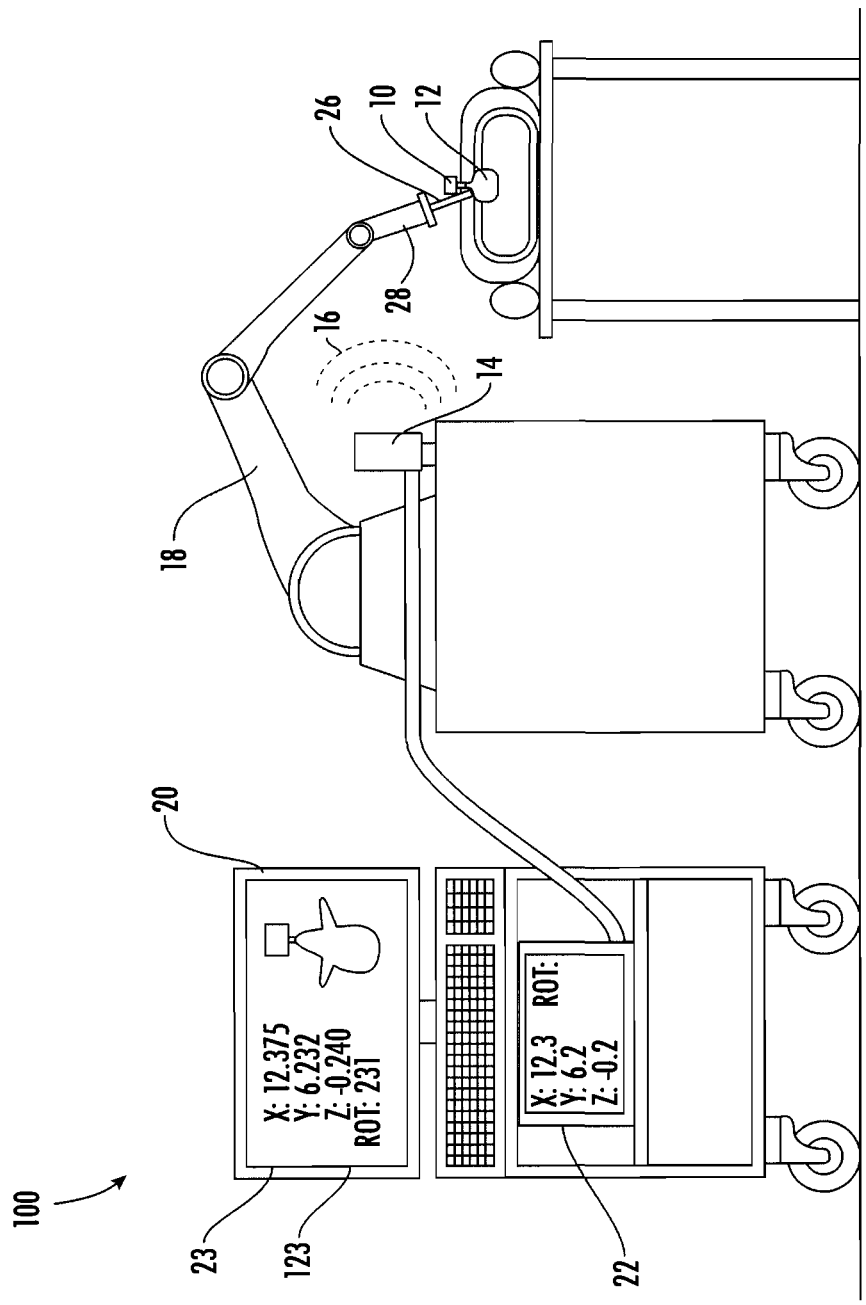
FIG. 2 is a schematic representation of one embodiment of the present invention.
Figure 3:
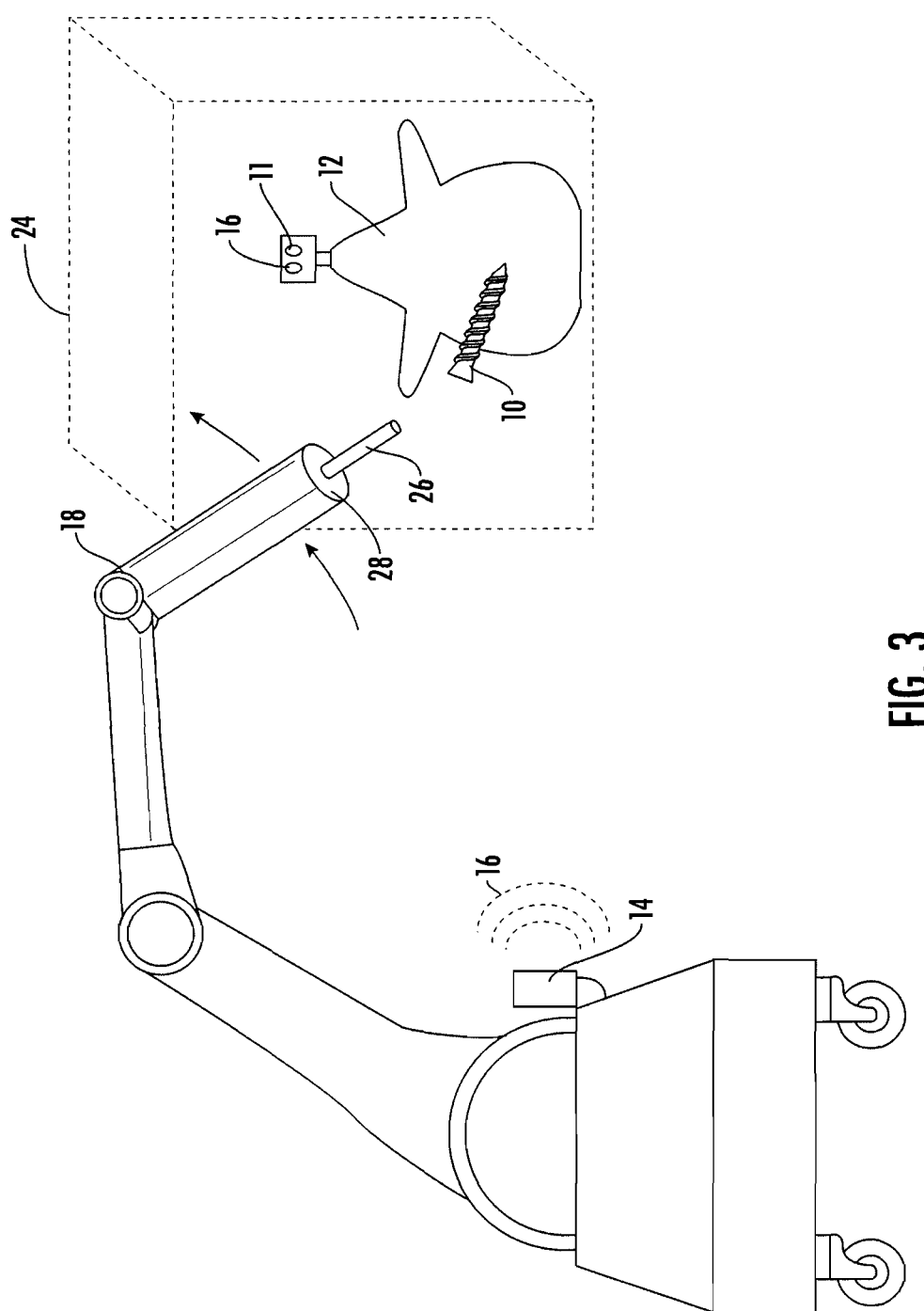
FIG. 3 is a partial schematic representation of the embodiment illustrated in FIG. 2.

Referring generally to FIGS. 1-3, a system and method 100 for compensating for static and dynamic positional interference in magnetic sensors during surgical procedures is illustrated. The system includes at least one electromagnetic sensor 10 secured rigidly to an object to be tracked, such as a bone 12. The electromagnetic sensor 10 may include a plurality of wire coils 11 positioned at different orientations with respect to each other for procuring electrical current when exposed to a magnetic field. A field generator 14 is constructed and arranged to induce electrical currents in the electromagnetic sensor 10 by producing a magnetic field 16 in proximity to the electromagnetic sensor 10. The field generator 14 is in electrical communication with the electromagnetic sensor 10, preferably by wired connection. It should be noted that while wired connection is preferable due to wire shielding and the like to produce a clear signal to the field generator 14, wireless connection may be possible without departing from the scope of the invention.

A robot 18 having at least two axes of movement, and more preferably six or seven axes of movement, such as an automotive style assembly robot, is electrically connected to a control computer 20 for controlling movements of said robot about the multiple axes of movement. The robotic control computer 20 is electrically connected to a system control unit 22 in electrical communication with the field generator 14 and the electromagnetic sensor(s) 10. The system control unit 22 is constructed and arranged to calculate the position and orientation of the electromagnetic sensor(s) 10 within a predetermined field 24 for receiving information regarding the position of the electromagnetic sensor(s) 10 for positioning the robot 18 and surgical tool 26. The surgical tool 26 is connected to the distal end 28 of the robot 18 for performing a portion of a medical procedure. The surgical tool 26 may be constructed of a material, such as metal, or some other material that interferes with the magnetic field when positioned within the predetermined field 24.

In alternative embodiments, the system may include multiple tools that are interchanged during the surgical procedure, either manually or automatically. In a preferred embodiment, the robot control computer 20 is utilized to cause the robot 18 to move the surgical tool 26 through a series of positions, recording positional interference between the electromagnetic sensor 10, the field generator 14, and the system control unit 22 to provide accurate positioning of said surgical tool 26 with respect to the electromagnetic sensor 10. In this manner, the positional interference is utilized during a surgical procedure by comparing the perceived surgical tool 26 position as controlled by the control computer 20 with the recorded positional interference to determine if the electromagnetic sensor 10 has moved with respect to an original position, requiring the robot to reposition its programmed moves to place it in proper relationship to the electromagnetic sensor 10. In at least some embodiments, the induced currents are varied by altering the magnetic field 16 with the field generator 14. In a preferred embodiment, the control computer 20 constructs a distortion map 23 for each surgical tool 26, the distortion map representing the positional distortion between the electromagnetic sensor(s) 10, the field generator 14, and the system control unit 22 for each surgical tool 26 as it is moved through a predetermined series of positions. In this manner, the real position of the electromagnetic sensor(s) 10 can be determined in real time without retracting the tool 26 from the operating site to remove the interference caused by the tool 26 entering the predetermined field 24.

In some embodiments, the surgical robot 18 utilizes two or more surgical tools 26 to complete an operation in these embodiments, each surgical tool 26 may be assigned a respective distortion map; so that, when a particular surgical tool 26 is utilized, the respective distortion map for the surgical tool 26 can be utilized for proper positioning of the surgical tool 26 for the procedure. In the preferred embodiment, the robot 18 moves the surgical tool 26 through a plurality of orientations and positions with respect to the electromagnetic sensor 10. In these embodiments, the positional distortion of the surgical tool 26 orientation may be stored on a second positional distortion map 123. In this manner, the first positional distortion map and the second positional distortion map may both be utilized to determine if the surgical tool 26 is being positioned as desired with respect to the electromagnetic sensor(s) 10 in real time. In a particularly preferred embodiment, the positions of the surgical tools 26 may be monitored as X, Y and Z coordinates, or they may be angular measurements of the robotic arms or any other suitable method of monitoring the distal position of a tool or a portion of the robotic arm itself.

Still referring to FIGS. 1-3, each sensor 10 preferably reports a full frame (full matrix of X, Y and Z coordinates, as well as rotation and angulation), which is used to determine the position of certain anatomical features to which the sensor is secured. As metal objects, such as surgical tools 26, are introduced into the sensor area of the predetermined field 24, the position and orientation values get skewed. This distorted value can be used to the advantage of the present system, as it defines a unique relationship between the sensor 10 and the medical or surgical tool 26. The present surgical system 100 looks at the difference between the ideal sensor position and the distorted sensor position. The system 100 will predict the distortion value for a sensor 10 given a known tool position/orientation, which can then be used to correct the sensor position data.

Implementation of the system 100 includes three main steps in the neural network. Test set collection, network training, and filtering. Test set collection involves a test collection program, which may be written in a computer language such as C++, and preferably a KUKA Sunrise Robot command program. The goal is to gather interference data that can be used to train the system. In one embodiment, an electromagnetic sensor from a company such as NDI is held in a substantially fixed position/orientation, while the surgical tool 26 is robotically moved around it via the command program and data is collected. This is repeated for many different sensor positions/orientations. The robot movements encompass as many different positions and orientations of the tool as possible with respect to the sensor or sensor's position. This will create the most training data for the system to learn with. As the robot is moving, tool position data is being sent to a test collection program.

The test collection program records an initial undistorted sensor matrix (the true sensor position). This sensor position is then locked for the remainder of the test run. The robot moves the tool through a series of test positions, causing distortion in the sensor data. This program records the distorted sensor data and current surgical tool 26 position. When the robot 18 finishes its movement patterns, for each recorded data point, this program calculates the difference between the original undistorted sensor and the distorted data. This value is the sensor distortion. The difference between the distorted sensor and undistorted sensor (X, Y, Z position and rotation matrix) becomes the values which the network will solve for. These results are written to the network and saved on the distortion map. This process is repeated with different sensor positions within a preferable six inch predetermined field 24. It should be noted that other predetermined field sizes can be utilized without departing from the scope of the invention. It should also be noted that by limiting the size of the field, the accuracy of the distortion map is increased.

The network training includes using the saved data from the test set collection. The network training program may be written in a computer programming language such as, but not limited to Python, and may train two networks which predict the position and orientation distortions for the sensor 10. The Python Program may be written using a computer programming language such as Google's TensorFlow API as the network framework. This program takes pre-saved training data and normalizes all values. Normalization is key in neural networks to avoid having large numbers skew training results. The normalization ranges are saved for later use in the live predictions. The data is split into Labels (the answer that we want the neural network to solve for) and features (the data which will be used to determine the labels). The Labels preferably include 12 values total (full matrix) which describe the distortion on the electromagnetic sensor. A features value includes nineteen (19) values which include the current tool Position and Euler Angles, the current electromagnetic sensor transformation matrix, and the electromagnetic sensor quality. The formatted training data is preferably passed to Google's TensorFlow API functions and saved to the neural network results. Preferably, two neural networks are trained; one calculates the positional distortion and one calculates the distortion on orientation. Training is repeated until the training loss (difference between provided label and predicted label) is preferably less than 0.01 mm and 0.01 degrees. Momentum based neural network is used to avoid getting stuck in local minima, and to aid in reaching a global minimum for training loss.

The Neural Network Live Feed includes a C++ and Python program, and uses the saved neural network to correct for distorted sensor data real time. The portion of the program written in C++ sends tool position data and raw electromagnetic sensor data to the neural network to be corrected, and corrects sensor data. This portion also receives and combines tool position data and raw electromagnetic sensor data and forwards this information to the Python Neural Network. The Python Neural Network receives distortion value back from the Python program for the current sensor. The difference between the raw sensor data and the distortion values received from the Python Neural Network (this is the corrected sensor position and orientation) is calculated. The corrected sensor data is forwarded to the sensor integration program.

The Python Program receives tool position/orientation data and sensor transformation data and supplies it to a neural network; and then sends the results back to the C++ program which receives the nineteen (19) features from the C++ program and normalizes them using the saved normalization values calculated during training. The normalized data is fed to the two saved neural networks and receives predicted distortion values. The predicted distortion values are combined and sent back to the C++ program.

What is claimed is:

1. A system for compensating for static and dynamic positional interference in magnetic sensors for surgical procedures comprising;

at least one electromagnetic sensor secured rigidly to an object to be tracked, wherein the object is a bone of a patient;

a field generator constructed and arranged to induce currents in said at least one electromagnetic sensor by producing a magnetic field in proximity to said at least one electromagnetic sensor, said field generator in electrical communication with said electromagnetic sensor;

a system control unit in electrical communication with said field generator and said at least one electromagnetic sensor, said system control unit calculating the position and orientation of said at least one electromagnetic sensor within a predetermined field;

a robot having at least two axes of movement, said robot electrically connected to a control computer for controlling movements of said robot along said at least two axes, said control computer electrically connected to said system control unit for receiving information regarding the position of said at least one electromagnetic sensor for positioning said robot with respect to said at least one sensor;

a surgical tool connected to said robot for performing a portion of a medical procedure, said surgical tool constructed of a material that interferes with said magnetic field when positioned within said predetermined field;

whereby said computer is utilized to cause said robot to move said surgical tool through a series of positions recording positional interference between said at least one electromagnetic sensor, said field generator and said system control unit to provide accurate positioning of said surgical tool with respect to said at least one electromagnetic sensor, and wherein the recorded positional interference is compared to a perceived surgical tool position to determine if the at least one electromagnetic sensor has moved with respect to an original position of the at least one electromagnetic sensor, and wherein the robot repositions the surgical tool to a proper position with respect to the electromagnetic sensor if the at least one electromagnetic sensor has moved with respect to an original position of the at least one electromagnetic sensor.

2. The system for compensating for static and dynamic positional interference in magnetic sensors of claim 1 wherein said robot includes three axes of movement.

3. The system for compensating for static and dynamic positional interference in magnetic sensors of claim 1 wherein said induced currents are varied by altering said magnetic field with said field generator.

4. The system for compensating for static and dynamic positional interference in magnetic sensors of claim 1 wherein said surgical tool includes metal.

5. The system for compensating for static and dynamic positional interference in magnetic sensors of claim 1 wherein said computer constructs a distortion map for said surgical tool, said distortion map representing said positional distortion between said at least one electromagnetic sensor and said field generator for said surgical tool as moved through said series of positions.

6. The system for compensating for static and dynamic positional interference in magnetic sensors of claim 5 wherein said robot utilizes two or more said surgical tools, each said tool including a respective distortion map.

7. The system for compensating for static and dynamic positional interference in magnetic sensors of claim 1 wherein said robot moves said surgical tool through a plurality of orientations with respect to said electromagnetic sensor.

8. The system for compensating for static and dynamic positional interference in magnetic sensors of claim 5 including two or more said electromagnetic sensors, said computer constructs a distortion map for said surgical tool and each said two or more sensors, said distortion map representing said positional distortion between said two or more electromagnetic sensors and said field generator for said surgical tool as moved through said series of positions.

9. The system for compensating for static and dynamic positional interference in magnetic sensors of claim 7 wherein positional distortion of said surgical tool orientation is stored on a second positional distortion map, said first positional distortion map and said second positional distortion map both utilized to determine if said surgical tool is being positioned as desired with respect to said electromagnetic sensor in real time.

10. The system for compensating for static and dynamic positional interference in magnetic sensors of claim 1 wherein said electromagnetic sensor includes a plurality of wire coils positioned at different orientations with respect to each other for procuring electrical current when exposed to said magnetic field.

* * * * *